(12) United States Patent
Harada et al.

(10) Patent No.: US 10,724,971 B2
(45) Date of Patent: Jul. 28, 2020

(54) DISPLAY DEVICE AND X-RAY CT DEVICE

(71) Applicant: Shimadzu Corporation, Kyoto (JP)

(72) Inventors: Daisuke Harada, Kyoto (JP); Shuhei Onishi, Kyoto (JP); Ryo Takahashi, Kyoto (JP); Yasuyuki Keyaki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 166 days.

(21) Appl. No.: 15/772,968

(22) PCT Filed: Nov. 5, 2015

(86) PCT No.: PCT/JP2015/081230
§ 371 (c)(1),
(2) Date: May 2, 2018

(87) PCT Pub. No.: WO2017/077627
PCT Pub. Date: May 11, 2017

(65) Prior Publication Data
US 2018/0328864 A1 Nov. 15, 2018

(51) Int. Cl.
*G01N 23/04* (2018.01)
*A61B 6/03* (2006.01)
(Continued)

(52) U.S. Cl.
CPC .......... *G01N 23/046* (2013.01); *A61B 5/7435* (2013.01); *A61B 6/032* (2013.01);
(Continued)

(58) Field of Classification Search
CPC ..... A61B 5/7435; A61B 6/032; A61B 6/4085; A61B 6/461; G01N 23/04; G01N 23/046; G06T 11/003; G06T 11/60; G06T 2200/24

See application file for complete search history.

(56) References Cited

U.S. PATENT DOCUMENTS

2006/0193437 A1 8/2006 Boeing et al.
2009/0122952 A1 5/2009 Nishide et al.
(Continued)

FOREIGN PATENT DOCUMENTS

CN 1813635 A 8/2006
JP 2009-112627 A 5/2009
(Continued)

OTHER PUBLICATIONS

Extended European Search Report dated Nov. 26, 2018, including the Supplementary European Search Report and the European Search Opinion, in connection with corresponding EP Application No. 15907813.8 (8 pgs.).

(Continued)

*Primary Examiner* — Mark R Gaworecki
(74) *Attorney, Agent, or Firm* — Maier & Maier, PLLC (57) ABSTRACT

A plurality of CT imaging conditions are created beforehand as presets, each preset is created beforehand as an icon, and each preset is associated with an icon and registered. Each icon is disposed in a CT imaging condition setting screen according to a spatial resolution and density resolution that serve as two-dimensional indexes relating to image quality. The selection of a given icon by a user results in the selection of the CT imaging conditions corresponding to the selected icon. The indexes relate to image quality and are two-dimensional, and this facilitates operation and makes it possible to intuitively select optimal CT imaging conditions with a small number of steps.

11 Claims, 5 Drawing Sheets

(51) Int. Cl.
*G06T 11/60* (2006.01)
*G06T 11/00* (2006.01)
*G01N 23/046* (2018.01)
*A61B 5/00* (2006.01)
*A61B 6/00* (2006.01)

(52) U.S. Cl.
CPC ............. *A61B 6/461* (2013.01); *G01N 23/04* (2013.01); *G06T 11/003* (2013.01); *G06T 11/60* (2013.01); *A61B 6/4085* (2013.01); *G06T 2200/24* (2013.01)

(56) References Cited

U.S. PATENT DOCUMENTS

| | | | | |
|---|---|---|---|---|
| 2014/0098931 | A1* | 4/2014 | Profio | A61B 6/03 378/19 |
| 2015/0141813 | A1* | 5/2015 | Kalafut | A61B 6/032 600/425 |

FOREIGN PATENT DOCUMENTS

| | | |
|---|---|---|
| JP | 2011-80971 A | 4/2011 |
| JP | 2015-000322 A | 1/2015 |
| WO | 98/16903 A1 | 4/1998 |
| WO | 2005/052866 A1 | 6/2005 |

OTHER PUBLICATIONS

International Search Report dated Jan. 12, 2016 of corresponding International Application No. PCT/JP2015/081230; 5 pgs.
Office Action dated Mar. 27, 2020 in corresponding Chinese Application No. 201580084328.9; 20 pages including English-language translation.

* cited by examiner

RESIN

| PRESET | ICON |
|---|---|
| PRESET 01 | ICON 01 |
| PRESET 02 | ICON 02 |
| ... | ... |
| PRESET 09 | ICON 09 |

LIGHT METAL

| PRESET | ICON |
|---|---|
| PRESET 11 | ICON 11 |
| PRESET 12 | ICON 12 |
| ... | ... |
| PRESET 19 | ICON 19 |

HEAVY METAL

| PRESET | ICON |
|---|---|
| PRESET 21 | ICON 21 |
| PRESET 22 | ICON 22 |
| ... | ... |
| PRESET 29 | ICON 29 |

FIG.5

DISPLAY DEVICE AND X-RAY CT DEVICE

FIELD

The present invention relates to a display device having a computer tomographic (CT) software function used in an X-ray CT device and an X-ray CT device having the same.

BACKGROUND

Typically, a display device (graphical user interface) having a CT software function is employed in an industrial X-ray CT device. Note that an X-ray radioscopic imaging device performs X-ray photography by obtaining a single piece of projection data, or by irradiating X-rays, sequentially obtaining a plurality of pieces of projection data, and displaying each of the projection data in real time (video display). Thus, by performing X-ray radioscopy, it is possible to check whether or not the projection data presents an optimum image by monitoring the image in the middle of the X-ray radioscopy. Therefore, even when an imaging condition is not suitable, the imaging condition can be changed in the middle of the X-ray radioscopy on the basis of the monitoring result.

In this regard, the X-ray CT device obtains a reconstructed image (CT image) by performing a reconstruction process using a plurality of pieces of projection data (for example, approximately 600 to 2,400 pieces of data). Therefore, unlike the X-ray radioscopic imaging device, when CT imaging is performed by the X-ray CT device, it is not possible to check whether or not the reconstructed image is optimum until the CT imaging and the reconstruction process are terminated. Therefore, when the CT imaging condition is not suitable, it is necessary to restart the CT imaging and the reconstruction process from the beginning. Even when the CT imaging is restarted, a user is not allowed to know whether or not the reset (changed) CT imaging condition is optimum before checking the reconstructed image obtained from the restarted imaging. In some cases, it is necessary to repeat the CT imaging over and over until an optimum reconstructed image is obtained.

In this regard, it is necessary to set an optimum CT imaging condition in advance before CT imaging. In the field of the X-ray CT device of the related art, a technique of setting an optimum CT imaging condition has been proposed (for example, see Patent Documents 1 and 2). Typically, when a user determines that the set CT imaging condition is optimum, the user performs an input operation for confirming the CT imaging condition by clicking an imaging condition input confirmation button displayed on a display screen of the graphical user interface (GUI). Then, the CT imaging is performed on the basis of the confirmed CT imaging condition.

In the field of the industrial X-ray CT device, the CT imaging is performed for various materials and structures with various image resolution requirements (such as a spatial resolution or a density resolution) and various imaging times. Therefore, since a wide variety of imaging conditions are set freely, the imaging conditions are to be set for each target object (work) as described below.

X-ray Condition: the X-ray condition includes a tube current or a tube voltage of an X-ray tube that generates X-rays.

Exposure Time: the exposure time is a net X-ray irradiation time.

Number of Views

Average Number: the number of views and the average number described above have the following relationship. Specifically, the "number of views" refers to an average number of scanned images for the same projection angle or for each projection angle including the vicinity of a target projection angle (that is, projection angles in the vicinity of the imaging time at the target projection angle), so that the number of scanned images required in the CT imaging becomes "number of views×average number". For example, when the number of views is set to "600" and the average number is set to "3", the number of scanned images necessary in the CT imaging becomes "1,800 (=600×3)". Note that, when the projection data are averaged at each projection angle including the vicinity of the target projection angle, the projection data at each projection angle are approximated to the projection data at the same angle as that of the target projection angle.

Slice Thickness

BH Correction Data Selection: the BH correction refers to "beam hardening correction". Note that the beam hardening correction herein refers to correction using image processing software (image processing algorithm).

Scaling Factor: the scaling factor herein refers to a response characteristic used in grayscale correction (also called "gamma correction").

In addition, the imaging condition includes a distance from a focal position to an X-ray detector (source-to-detector distance: SDD) in a vertical direction when the vertical line is drawn from the focal position of the X-ray tube to the X-ray detector, a distance from the focal position of the X-ray tube to a rotation center of the target object (source-to-rotation-center distance: SRD), a CT imaging mode (such as cone beam CT (CBCT)), a scan count, a total scan time, and the like.

Patent Document 1: JP-A-2009-112627
Patent Document 2: JP-A-2011-080971

SUMMARY

However, the imaging condition setting has a lot of items and takes long time disadvantageously. In addition, when a user who does not fully understand (who is not sufficiently experienced in) an industrial X-ray CT device performs the imaging condition setting, it is difficult to determine which setting is optimum.

In view of the aforementioned problems, an object of the invention is to provide a display device and an X-ray CT device having a CT software function that enables an intuitive setting of an optimum CT imaging condition through a small number of steps with excellent operability.

In order to achieve the aforementioned object, according to an aspect of the invention, there is provided a display device having a computer tomographic (CT) software function used in an X-ray CT device, including control elements configured to register presets for a plurality of CT imaging conditions and arranged on a display screen using a two-dimensional index relating to image quality, wherein, as one of the control elements is selected, a CT imaging condition corresponding to the selected control element is set.

In the display device according to the invention, a plurality of CT imaging conditions are created in advance as presets, and each preset is registered by mating with each control element. Each control element is arranged on the display screen using a two-dimensional index relating to image quality. As a user selects any control element, a CT imaging condition corresponding to the selected control element is selected. The index relates to image quality and is two-dimensional. Therefore, even a user who does not fully understand the CT imaging condition can intuitively select and set an optimum CT imaging condition through a small number of steps just by visually checking and selecting the control element. In addition, in a case where new image quality improvement is required after CT imaging, and the imaging is restarted, what is selected for the required image quality becomes clear. Therefore, it is possible to easily change the CT imaging condition. As a result, it is possible to intuitively set an optimum CT imaging condition through a small number of steps with excellent operability.

Herein, the control element refers to a virtual tool of a graphical user interface (GUI) and is also called "Widget". A control element for the input setting including selection includes, for example, an icon, a dropdown list, a combobox, a radio button, a checkbox, a tap, or the like.

The icon is displayed by symbolizing an object with a simple pictogram. The dropdown list allows a user to select one of the values from the list. The combobox allows a user to directly input a value and select the value from existing options. The radio button is also called an "option button" and is used to select one of the options defined in advance. As one of the radio buttons is selected (pressed), a button selected (pressed) previously returns to a non-selection (not pressed) state, so that only one of buttons is selected (pressed) at all times. The checkbox is used to select a plurality of items from several options. The tap is used to switchably display a document so that the managed document is switchably displayed by selecting the tap.

The index of the display device according to the invention described above includes, for example, a spatial resolution and a density resolution (that is, contrast). As a user selects any control element corresponding to any one of the spatial resolution and the density resolution, a CT imaging condition corresponding to the selected control element is selected. The index includes the spatial resolution and the density resolution relating to image quality and is two-dimensional. Therefore, even a user who does not fully understand the CT imaging condition can intuitively select and set an optimum CT imaging condition through a small number of steps just by visually checking and selecting the control element. In addition, in a case where the imaging is restarted as new image quality improvement is required after the CT imaging, what is selected for the spatial resolution or the density resolution to match the required image quality becomes clear. Therefore, it is possible to easily change the CT imaging condition. As a result, it is possible to intuitively set an optimum CT imaging condition through a small number of steps with excellent operability by selecting a control element corresponding to at least one of the spatial resolution or the density resolution.

In the display device described above according to the invention, when the CT imaging condition is selected, a preview image is preferably displayed as an image view serving as a reference of the output image corresponding to the selected condition. By displaying the preview image as an image view serving as a reference of the output image corresponding to the selected condition, it is possible to display the preview image as an image view regarding what type of output image is obtained from the selected condition and display how the output image is changed for the selected CT imaging condition. In addition, it is possible to check what type of output image is obtained from the preview image without performing the CT imaging or the reconstruction process.

In the display device described above according to the invention, it is preferable to arrange the control elements as icons side by side in horizontal and vertical directions for each index on the display screen. As described above, since the icon is displayed by symbolizing an object with a simple pictogram, a user can easily recognize the icon and more intuitively set an optimum CT imaging condition.

In the display device described above according to the invention, the control elements may be displayed independently for each index. For example, in a case where the index includes the spatial resolution (simply, resolution) and the density resolution (contrast), a setting combination of the resolution and the contrast may be set for each imaging condition.

The display device described above according to the invention preferably further includes imaging condition display means configured to display the set CT imaging condition. The CT imaging condition may be corrected immediately by checking the set CT imaging condition.

The display device described above according to the invention further includes imaging condition input confirmation means configured to perform an input operation for confirming the set CT imaging condition, wherein CT imaging is performed on the basis of the confirmed CT imaging condition in response to the input operation to the imaging condition input confirmation means. When a user determines that the set CT imaging condition is optimum, an input operation is performed on the imaging condition input confirmation means, so that the input operation for confirming the CT imaging condition is performed. In addition, CT imaging is performed on the basis of the confirmed CT imaging condition.

The display device described above according to the invention preferably further includes a control element that enables selection of a material on the display screen, wherein, when the control element is selected, a CT imaging condition is set for each material corresponding to the selected control element. A control element is further provided for each material and is arranged to match the two-dimensional index relating to image quality. All parameters necessary to set the CT imaging condition corresponding to the index and the material are set by selecting the control element. Therefore, even a user who does not fully understand the CT imaging condition can select an optimum CT imaging condition from the material of the target object (work) and the obtained image quality.

In the display device described above according to the invention, the control element that enables selection of the material includes, for example, a dropdown list, a combobox, a radio button, a checkbox, or a tap. By configuring the control element that enables selection of the material using the dropdown list, the combobox, the radio button, the checkbox, or the tap, it is possible to allow a user to easily select the control element that enables selection of the material and select an optimum CT imaging condition on the basis of the material and the image quality.

In the display device described above according to the invention, a preset of the registered CT imaging condition may be configured editably. In this configuration, for example, a user can arbitrarily change or add the preset, can arbitrarily change the content of the material to be selected, or can arbitrarily add the type of the material.

The display device described above according to the invention may be applied to an X-ray CT device.

Specifically, according to the invention, there is provided an X-ray CT device including: an X-ray source that generates an X-ray for irradiating X-rays onto a target object; a stage for placing the target object; an X-ray detector that detects the X-ray irradiated from the X-ray source to the target object and transmitted through the target object; the display device according to any one of claims 1 to 10, the display device having a CT software function including a function of setting a CT imaging condition; and a reconstruction processing unit that reconstructs a CT image of the target object from the data detected by the X-ray detector.

The X-ray CT device according to the invention has the display device according to the invention that enables an intuitive setting of an optimum CT imaging condition through a small number of steps with excellent operability. Therefore, it is possible to set an optimum CT imaging condition in advance before the CT imaging. Therefore, it is not necessary to restart the CT imaging. In addition, even when the CT imaging condition is not suitable, it is possible to reset (change) the CT imaging condition before the CT imaging by displaying, for example, the preview image. Therefore, it is not necessary to repeat the CT imaging over and over until an optimum reconstructed image is obtained.

In the display device according to the invention, a plurality of CT imaging conditions are created as presets in advance, and each preset is registered by mating with each control element. Each control element is arranged on the display screen using a two-dimensional index relating to image quality. As a user selects any control element, a CT imaging condition corresponding to the selected control element is selected. The index relates to image quality and is two-dimensional. Therefore, it is possible to intuitively set an optimum CT imaging condition through a small number of steps with excellent operability just by visually checking and selecting the control element.

The X-ray CT device according to the invention has the display device according to the invention, that enables an intuitive setting of an optimum CT imaging condition through a small number of steps with excellent operability. Therefore, it is possible to set an optimum CT imaging condition in advance before the CT imaging.

DETAILED DESCRIPTION OF THE DRAWINGS

Figure 1:
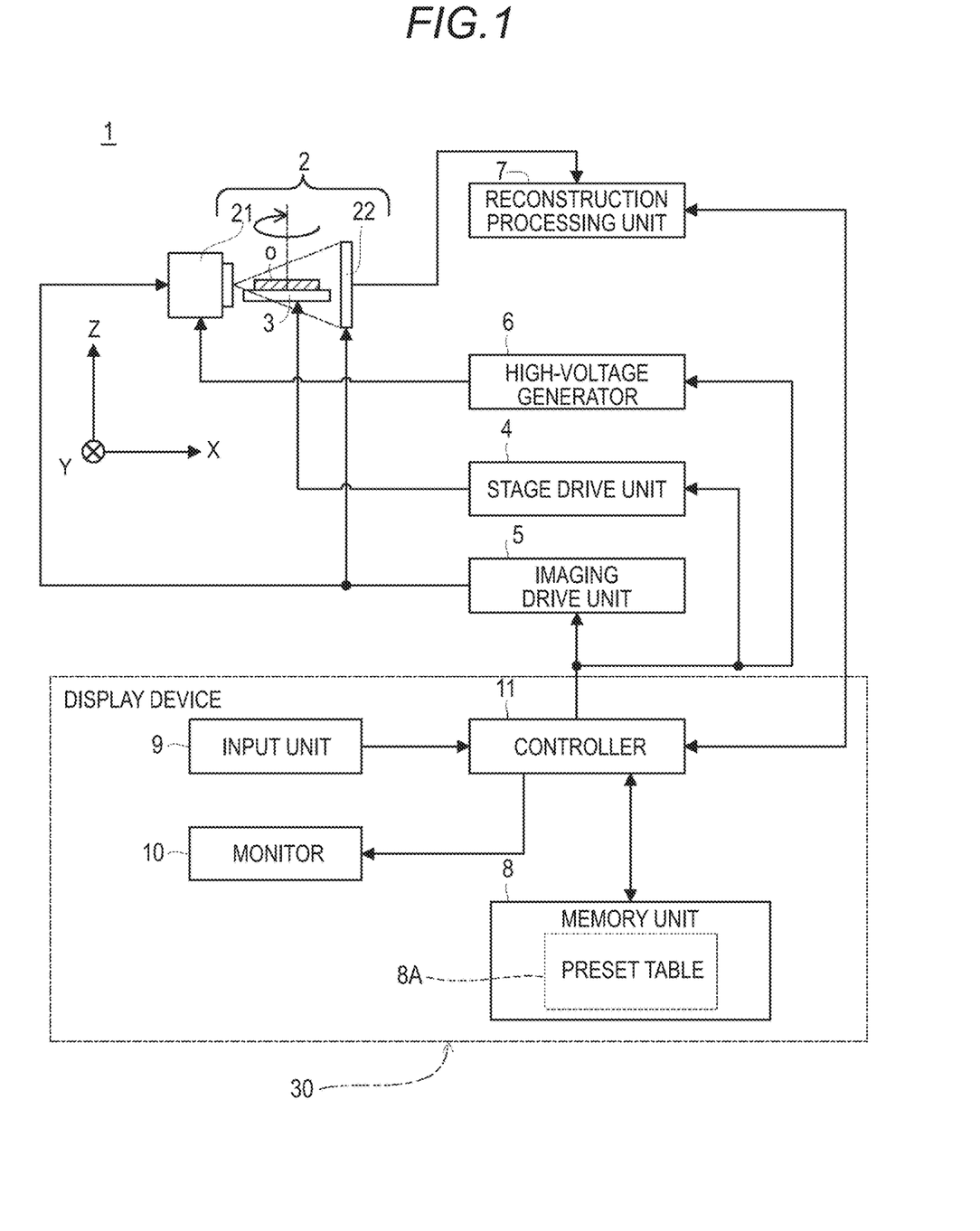
FIG. 1 is a schematic diagram illustrating an X-ray CT device along with a block diagram illustrating a display device according to an embodiment of the invention.

Embodiments of the invention will now be described with reference to the accompanying drawings. FIG. 1 is a schematic diagram illustrating an X-ray CT device along with a block diagram of the display device according to an embodiment of the invention.

As illustrated in FIG. 1, the X-ray CT device 1 according to the embodiment includes an imaging unit 2 that images a target object O, a stage 3 for placing the target object O, a stage drive unit 4 that drives the stage 3, an imaging drive unit 5 that drives the imaging unit 2, a high-voltage generator 6 that generates a high voltage in order to supply a tube current or a tube voltage to an X-ray tube 21 of the imaging unit 2, and a reconstruction processing unit 7 that perform a reconstruction process for the projection data obtained by the X-ray detector 22 of the imaging unit 2.

The imaging unit 2 includes an X-ray tube 21 that irradiates X-rays onto the target object O, and an X-ray detector 22 that detects X-rays irradiated from the X-ray tube 21 and transmitted through the target object O. Any type of device such as an image intensifier (I.I) or a flat panel type X-ray detector (FPD: Flat Panel Detector) may be employed as the X-ray detector 22 without any particular limitation. In this embodiment, it is assumed that a flat panel type X-ray detector (FPD) is employed as the X-ray detector 22. The X-ray tube 21 corresponds to an X-ray source according to the invention.

The FPD has a plurality of detection elements arranged side by side across horizontal and vertical directions by mating with pixels, and the detection element detects an X-ray, so that data (electric charge signal) on the detected X-rays are output as an X-ray detection signal. As a result, an X-ray is irradiated from the X-ray tube 21 to the target object O, and the X-ray detector 22 such as the FPD detects the X-ray and outputs an X-ray detection signal. In addition, projection data are obtained by arranging pixel values based on the X-ray detection signal to match pixels (detection elements).

The stage drive unit 4 includes a motor, a drive shaft, or the like (not illustrated) to rotate the stage 3 on a horizontal plane around a Z-axis center in the drawing. By virtue of rotation of the stage 3 on the horizontal plane, the target object O also rotates around the Z-axis center on the horizontal plane, so that a plurality of pieces of projection data are obtained.

Similar to the stage drive unit 4, the imaging drive unit 5 includes a motor, a drive shaft, or the like (not illustrated). The X-ray CT imaging is performed by shifting the X-ray detector 22 or the X-ray tube 21 to face each other. In addition, a magnification ratio of the X-ray CT imaging may be changed by horizontally shifting the X-ray tube 21 or the X-ray detector 22 (X-direction in the drawings). In addition, the target object O may be scanned from an inclined direction by sloping the X-ray tube 21 or the X-ray detector 22 with respect to the X-axis.

The high-voltage generator 6 generates a high voltage and applies the tube current or the tube voltage to the X-ray tube 21 to generate X-rays from the X-ray tube 21 and irradiate the X-rays to the target object O. The reconstruction processing unit 7 executes a reconstruction process well know in the art, such as a filtered back projection (FBP) method, a successive approximation method, or a combination thereof, using a plurality of projection data to obtain a reconstructed image for the target object O.

The display device 30 having a CT software function used in the X-ray CT device 1 has a memory unit 8, an input unit 9, a monitor 10, and a controller 11. In addition, as a manipulation environment for an operator (user), the display device 30 has a graphical user interface (GUI).

Using the controller 11, data such as the projection data obtained by the X-ray detector 22 or the reconstructed image obtained by the reconstruction processing unit 7 are written and stored in the memory unit 8, are appropriately read as necessary, so that the projection data or the reconstructed image is transmitted and output to the monitor 10. The memory unit 8 includes a storage medium such as a read-only memory (ROM), a random-access memory (RAM), or a hard disk.

In addition, according to this embodiment, the memory unit 8 has a preset table 8A regarding icons and presets registered for the icons. When the CT imaging condition is set, the icons stored in the preset table 8A and the presets for a plurality of CT imaging conditions are read onto the display screen of the monitor 10 (that is, the CT imaging condition setting screen 10A of FIG. 2) using the controller 11.

In this manner, the display device 30 is configured such that the icons for which presets for a plurality of CT imaging conditions are registered are arranged on the display screen of the monitor 10 (the CT imaging condition setting screen 10A of FIG. 2) along with a spatial resolution and a density resolution as a two-dimensional index relating to image quality. In addition, the display device 30 is configured such that a CT imaging condition corresponding to the selected icon is set by selecting icon. The CT imaging condition setting will be described below in more details.

The input unit 9 transmits data or a command input from a user to the controller 11. The input unit 9 includes a keyboard and a pointing device such as a mouse, a joystick, a track ball, and a touch panel.

The monitor 10 is configured to display a screen for setting the CT imaging condition (that is, the CT imaging condition setting screen 10A of FIG. 2) according to this embodiment. In addition, the projection data or the reconstructed image is displayed on the monitor 10 after the CT imaging. The CT imaging condition setting screen will also be described below in more details.

The controller 11 comprehensively controls each part of the X-ray CT device 1 and the display device 30. As described above, when the CT imaging condition is set, the icons stored in the preset table 8A and the presets for a plurality of CT imaging conditions are read onto the display screen of the monitor 10 using the controller 11. In addition, an input operation for confirming the CT imaging condition is performed as a user clicks the imaging condition input confirmation button 10f (refer to FIG. 2). In order to perform the CT imaging based on the confirmed CT imaging condition, a control command based on the CT imaging condition is transmitted from the controller 11 to the stage drive unit 4, the imaging drive unit 5, or the high-voltage generator 6. Note that, after the CT imaging is performed, data such as the projection data obtained by the X-ray detector 22 or the reconstructed image obtained by the reconstruction processing unit 7 are written or stored in the memory unit 8 using the controller 11, or are transmitted and output to the monitor 10 for display.

According to this embodiment, the reconstruction processing unit 7 or the controller 11 includes a central processing unit (CPU) or the like. Note that the reconstruction processing unit 7 may also include a graphic processing unit (GPU) or the like.

Figure 2:
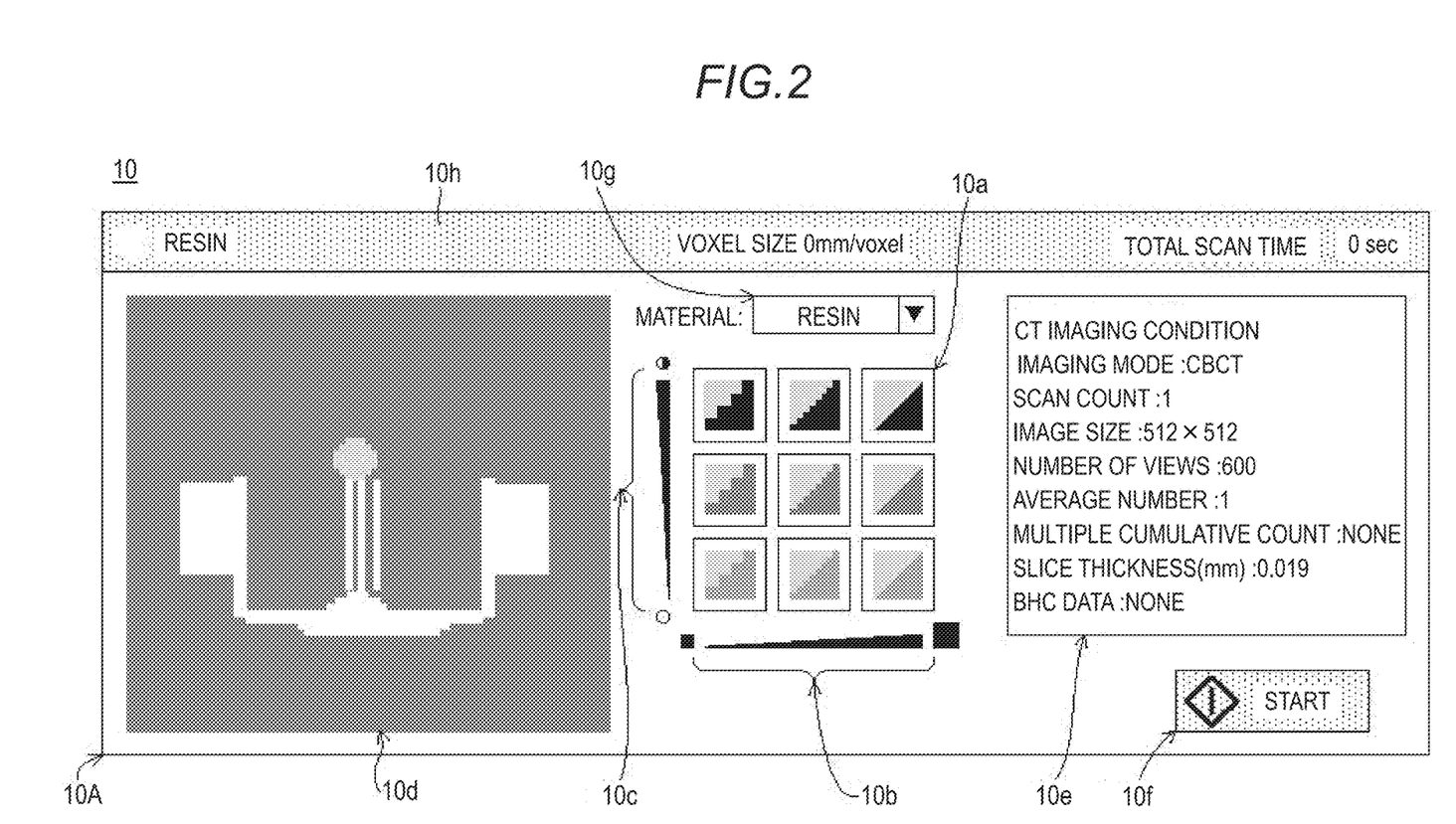
FIG. 2 illustrates a CT imaging condition setting screen of the display device according an embodiment of the invention.
Figure 3:
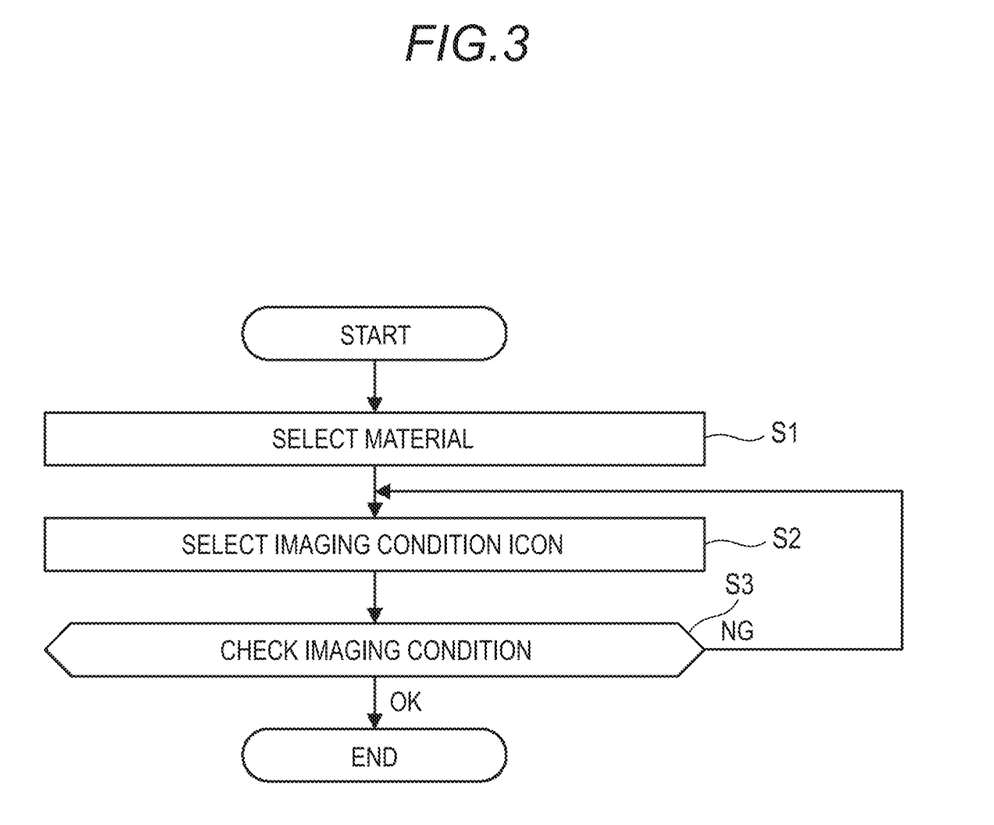
FIG. 3 is a flowchart illustrating a CT imaging condition setting process according to an embodiment of the invention.
Figure 4:
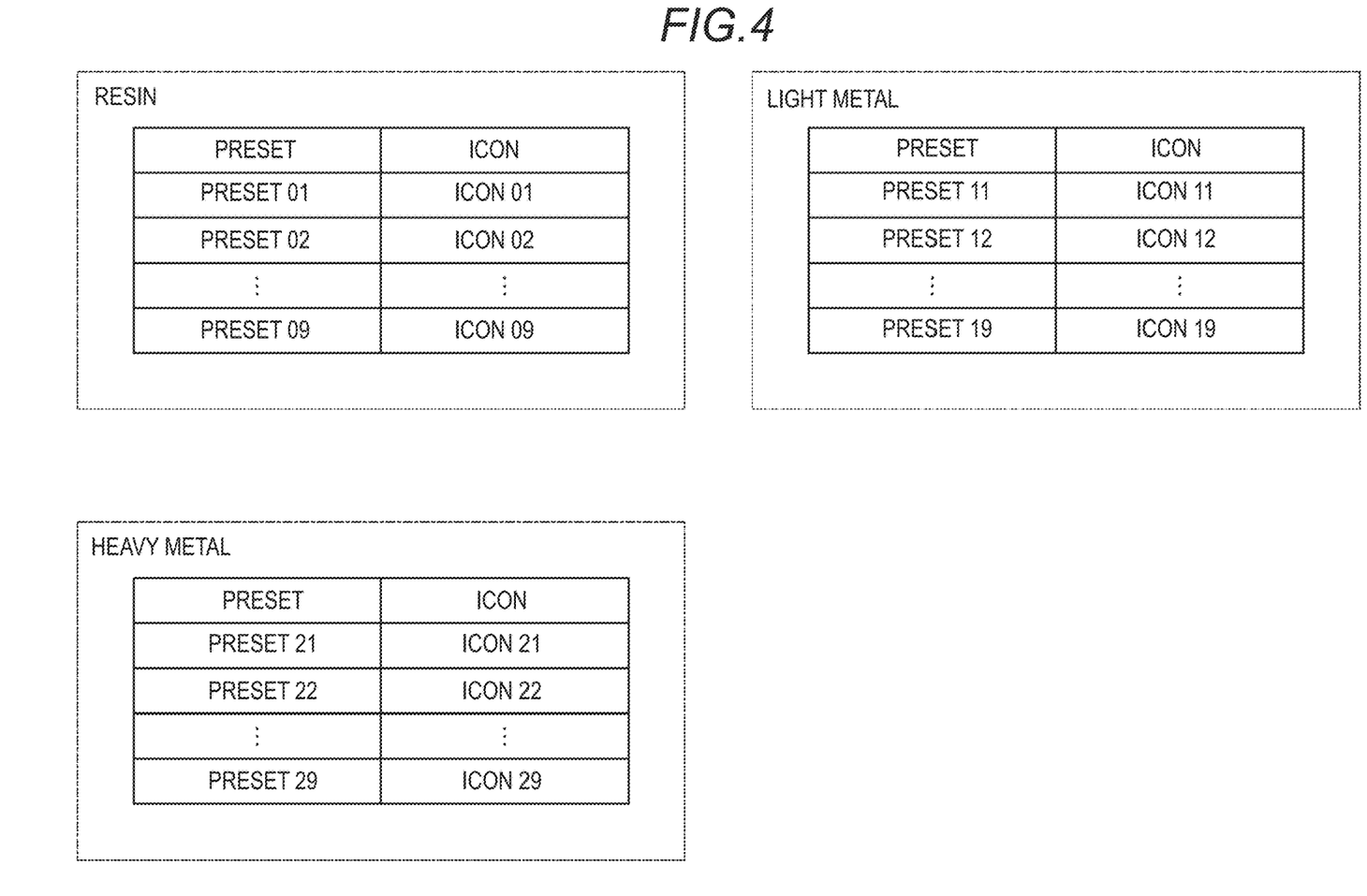
FIG. 4 illustrates a table containing icons and presets registered for the icons according to an embodiment of the invention.

Next, the CT imaging condition setting will be described with reference to FIGS. 2 to 4. FIG. 2 illustrates a type of the CT imaging condition setting screen on the display device according to an embodiment of the invention. FIG. 3 is a flowchart illustrating the CT imaging condition setting according to an embodiment of the invention. FIG. 4 illustrates icons and a type of the table regarding presets registered for the icons.

As illustrated in FIG. 2, the monitor 10 is configured to display the CT imaging condition setting screen 10A (display screen) on which a plurality of icons 10a (nine icons in FIG. 2) are arranged. A plurality of CT imaging conditions (nine conditions in this embodiment) are created in advance as presets, and the presets are registered by mating with the icons 10a one by one. Each icon 10a is arranged on the CT imaging condition setting screen 10A (display screen) using the two-dimensional index regarding image quality.

According to this embodiment, the index includes a spatial resolution (that is, CT image size) 10b and a density resolution (contrast) 10c. The icons 10a are arranged side by side across horizontal and vertical directions on the CT imaging condition setting screen 10A (display screen) for each index (including the spatial resolution 10b and the density resolution 10c). In FIG. 2, the icons 10a are arranged in a 3×3 matrix shape along horizontal and vertical axes by setting the horizontal axis to the spatial resolution 10b and setting the vertical axis to the density resolution 10c.

Note that an icon representing the imaging time may be displayed along with each of the icons 10a by mating with the presets. As a user selects any icon 10a by clicking, for example, on a mouse, the selected icon 10a is preferably highlighted (for emphasis) in order to distinguish the selected icon 10a from other remaining icons 10a.

When the CT imaging condition is selected, a preview image 10d is displayed as an image view serving as a reference of the output image corresponding to the selected condition. There is no particular limitation to the image view. For example, a reconstructed image obtained in advance may be used as the image view, or a photograph or a schematic diagram may also be used as the image view.

An imaging condition display unit 10e for presenting the set CT imaging condition is displayed on the CT imaging condition setting screen 10A (display screen). In FIG. 2, the imaging condition display unit 10e is displayed in the right side of the CT imaging condition setting screen 10A (display screen). However, the display position of the imaging condition display unit 10e is not particularly limited. Note that "SCAN COUNT" of FIG. 2 refers to frequency of performing the CT imaging by changing the height of the target object (work), and "MULTIPLE CUMULATIVE COUNT" refers to frequency of performing CT imaging for the same position. "BHC DATA" refers to the beam hardening correction data. The imaging condition display unit 10e corresponds to "imaging condition display means" according to the invention.

An imaging condition input confirmation button 10f ("START" in FIG. 2) is displayed on the CT imaging condition setting screen 10A (display screen). The imaging condition input confirmation button 10f corresponds to "imaging condition input confirmation means" according to the invention. The "START" button of FIG. 2 also has a function of starting execution of the CT imaging, so that the CT imaging starts as this button is pressed.

A dropdown list 10g that allows a user to select a material of the imaging target is displayed on the CT imaging condition setting screen 10A (display screen). In FIG. 2, "RESIN" is selected as a material. Alternatively, for example, light metals, heavy metals, electronic/electric components, and the like may be displayed as a list on the dropdown list 10g, so that a user can select one of them including the resin.

In addition, an item 10h is displayed on the CT imaging condition setting screen 10A (display screen). In FIG. 2, the item 10h is displayed in the upper side of th CT imaging condition setting screen 10A (display screen). However, the display position of the item 10h is not particularly limited. Furthermore, the content displayed on the item 10h is not particularly limited. For example, as illustrated in FIG. 2, the selected material ("RESIN" in FIG. 2) is displayed in the left side of the item 10h, the set spatial resolution (CT image size) ("PIXEL SIZE" in FIG. 2) is displayed in the center of the item 10h, and the set total scan time is displayed in the right side of the item 10h.

The imaging condition is roughly determined as illustrated in the flowchart of FIG. 3. First, a material is selected (step S1). Then, an icon suitable for a purpose is selected from the imaging condition icons arranged two-dimensionally (step S2). As a result, individual imaging conditions are displayed on the imaging condition display unit. Therefore, a user checks the individual imaging conditions (step S3). If the imaging condition is suitable, the imaging condition setting is terminated. If the condition is not suitable, the process returns to step S2, so that an imaging condition icon is selected again. When a part of the imaging conditions are changed, the conditions displayed on the imaging condition display unit may also be directly changed.

The imaging condition setting will be described by way of example. In this example, it is assumed that the material is set to "RESIN". As illustrated in FIG. 4, PRESET 01 is registered by mating with ICON 01. Similarly, PRESET 02 is registered by mating with ICON 02, and so on. Finally, as PRESET 09 is registered by mating with ICON 09, a table is created by registering nine PRESETs 01 to 09 by mating with ICONs 01 to 09, respectively, for each resin. Similarly, as another material, a table is created by registering nine PRESETs 11 to 19 by mating with ICONs 11 to 19, respectively, for each light metal, and a table is created by registering nine PRESETs 21 to 29 by mating with ICONs 21 to 29, respectively, for each heavy metal. This table creation process is performed as a factory setting performed in advance when the device is shipped in a factory. Therefore, an operator is not necessary to create the table individually.

(Step S1) Selection of Material

A material is selected from a target object (work) to be scanned. For example, assuming that the target object is formed of resin, a user selects "RESIN" from the list by clicking the dropdown list 10g (refer to FIG. 2). The table (refer to FIG. 4) stored in the preset table 8A (refer to FIG. 1) and obtained by registering nine PRESETS 01 to 09 mated with ICONs 01 to 09, respectively, for each resin is read onto the CT imaging condition setting screen 10A (refer to FIG. 2).

(Step S2) Selection of Imaging Condition Icon

A user selects the corresponding one from the icons 10a arranged on the CT imaging condition setting screen 10A (display screen) (refer to FIG. 2). The CT imaging condition corresponding to the selected icon is displayed on the imaging condition display unit 10e (refer to FIG. 2). In this case, a preview image 10d is displayed (refer to FIG. 2), and the spatial resolution of the CT imaging condition or the total scan time is displayed on the item 10h (refer to FIG. 2).

(Step S3) Confirmation of Imaging Condition

A user checks the imaging condition on the basis of the CT imaging conditions (such as the imaging time or the resolution) displayed on the preview image 10d and the imaging condition display unit 10e.

If a user determines that the imaging condition is not suitable ("NG" in FIG. 3), the process returns to step S2. If a user determines that the imaging condition is optimum ("OK" in FIG. 3), a user confirms the corresponding CT imaging condition by clicking the imaging condition input confirmation button 10f (refer to FIG. 2), and a series of imaging condition settings are terminated ("END" in FIG. 3).

As the START button 10f displayed in FIG. 2 is pressed, a control command based on the CT imaging condition determined in steps S1 to S3 of FIG. 3 is transmitted from the controller 11 (refer to FIG. 1) to the stage drive unit 4 (refer to FIG. 1), the imaging drive unit 5 (refer to FIG. 1), or the high-voltage generator 6 (refer to FIG. 6), so that the CT imaging is performed on the basis of the CT imaging condition.

In the display device 30 according to this embodiment, a plurality of CT imaging conditions are created in advance as presets, and each preset is created in advance as a control element (icons 10a in FIG. 2), so that each preset is registered by mating with each control element (icons 10a). Each control element (icons 10a) is arranged on the display screen (the CT imaging condition setting screen 10A in FIG. 2) with a two-dimensional index (the spatial resolution 10b and the density resolution 10c in FIG. 2 in this embodiment). As a user selects any control element (icons 10a), the CT imaging condition corresponding to the selected control element (icon 10a) is selected. The index relates to image quality and is two-dimensional. Therefore, even a user who does not fully understand the CT imaging condition can intuitively select and set an optimum CT imaging condition through a small number of steps just by visually checking and selecting a control element (icon 10a). In addition, in a case where the imaging is restarted as new image quality improvement is required after the CT imaging, what is selected for the required image quality becomes clear. Therefore, it is possible to easily change the CT imaging condition. As a result, it is possible to intuitively set an optimum CT imaging condition through a small number of steps with excellent operability.

Here, the control element herein refers to a virtual tool of a graphical user interface (GUI) as described above in "Summary of the Invention" and is also called "Widget". As a control element for the input setting including selection, according to this embodiment, the icons 10a are employed as illustrated in FIG. 2. As described above, the icon 10a is displayed by symbolizing an object with a simple pictogram.

According to this embodiment, as illustrated in FIG. 2, the index includes the spatial resolution (CT image size) 10b and the density resolution (contrast) 10c. As a user selects any control element (icon 10a) corresponding to at least one of the spatial resolution and the density resolution, the CT imaging condition corresponding to the selected control element (icon 10a) is selected. Since the index is two-dimensional and includes the spatial resolution 10b and the density resolution 10c relating to image quality, even a user who does not fully understand the CT imaging condition can intuitively select and set an optimum CT imaging condition through a small number of steps just by visually checking and selecting the control element (icon 10a). In addition, in a case where the imaging is restarted as new image quality improvement is required after the CT imaging, what is selected for the spatial resolution 10b or the density resolution 10c required for the image becomes clear. Therefore, it is possible to easily change the CT imaging condition. As a result, it is possible to intuitively set an optimum CT imaging condition through a small number of steps with excellent operability by selecting the control element (icon 10a) corresponding to at least one of the spatial resolution 10b and the density resolution 10c.

As illustrated in FIG. 2, when the CT imaging condition is selected, a preview image 10d is preferably displayed as an image view serving as a reference of the output image corresponding to the selected condition. By displaying the preview image 10d as an image view serving as a reference of the output image corresponding to the selected condition, it is possible to display the preview image as an image view regarding what type of output image is obtained from the selected condition and display how the output image is changed for the selected CT imaging condition. In addition, it is possible to check what type of output image is obtained from the preview image 10d without performing the CT imaging or the reconstruction process.

It is preferable to arrange the icons 10a as the control elements side by side in horizontal and vertical directions for each index (spatial resolution 10b and density resolution 10c) on the display screen (CT imaging condition setting screen 10A) as illustrated in FIG. 2. As described above, since the icon 10a is displayed by symbolizing an object with a simple pictogram, a user can easily recognize the icon 10a and more intuitively set an optimum CT imaging condition.

It is preferable to provide imaging condition display means (imaging condition display unit 10e in FIG. 2) for displaying the set CT imaging condition as illustrated in FIG. 2. The CT imaging condition may be corrected immediately by checking the set CT imaging condition.

As illustrated in FIG. 2, imaging condition input confirmation means used to confirm the set CT imaging condition (the imaging condition input confirmation button 10f of FIG. 2) is provided so that CT imaging is performed on the basis of the confirmed CT imaging condition in response to an input operation of the imaging condition input confirmation means (imaging condition input confirmation button 10f). When a user determines that the set CT imaging condition is optimum, an input operation is performed on the imaging condition input confirmation means (imaging condition input confirmation button 10f), so that the input operation for confirming the CT imaging condition is performed. In addition, CT imaging is performed on the basis of the confirmed CT imaging condition.

It is preferable to further provide a control element that enables selection of a material (the dropdown list 10g of FIG. 2 in this embodiment), so that the CT imaging condition is set for each material corresponding to the selected control element (dropdown list 10g) when the control element (dropdown list 10g) is selected. A control element (dropdown list 10g) is further provided for each material, and the control element (dropdown list 10g) is arranged to match the two-dimensional index (including the spatial resolution 10b and the density resolution 10c) relating to the image quality. By selecting the control element (dropdown list 10g), both the index (including spatial resolution 10b and the density resolution 10c) and the parameter necessary to set the CT imaging condition corresponding to the material are wholly set. Therefore, even a user who does not fully understand the CT imaging condition can select an optimum CT imaging condition from the material of the target object (work) and the obtained image quality.

According to this embodiment, the aforementioned control element that enables selection of the material is the dropdown list 10g as illustrated in FIG. 2. By configuring the control element that enables selection of the material using the dropdown list 10g, it is possible to allow a user to easily select the control element that enables selection of the material and select an optimum CT imaging condition from the material and the image quality. The dropdown list 10g allows a user to select one of the values from the list.

The X-ray CT device 1 according to this embodiment has the display device 30 according to this embodiment that enables an intuitive setting of an optimum CT imaging condition through a small number of steps with excellent operability.

Therefore, it is possible to set an optimum CT imaging condition in advance before the CT imaging. Therefore, it is not necessary to restart the CT imaging. In addition, even when the CT imaging condition is not suitable, it is possible to reset (change) the CT imaging condition before CT imaging by displaying, for example, the preview image 10d as in this embodiment. Therefore, it is not necessary to repeat the CT imaging over and over until an optimum reconstructed image is obtained.

The invention may be modified as follows without limiting to the aforementioned embodiment.

(1) In the aforementioned embodiment, the control element (icon 10a in the aforementioned embodiment) is selected by clicking a mouse, and the material is selected from the list by clicking the dropdown list 10g (refer to FIG. 2). Alternatively, by configuring the input unit 9 (refer to FIG. 1) using a touch panel, the monitor 10 (refer to FIG. 1) also functions as the input unit 9, so that a user may select the control element on the touch panel by pressing the control element with a finger.

(2) In the aforementioned embodiment, the imaging mode is set as illustrated in FIG. 1. Alternatively, any tomographic mode such as tomosynthesis may also be employed without a limitation.

(3) In the aforementioned embodiment, as the control element in which the presets for a plurality of CT imaging conditions are registered, the icons 10a are employed as illustrated in FIG. 2. Alternatively, any control element such as the dropdown list 10g of FIG. 2 may also be employed as long as it is used to perform an input setting including selection. Alternatively, as a control element for performing the input setting including selection, for example, a combobox, a radio button, a checkbox, a tap, or the like may also be employed. The combobox allows a user to directly input a value and select the value from existing options. The radio button is also called an "option button" and is used to select one of the options defined in advance. As one of the radio buttons is selected (pressed), a button selected (pressed) previously returns to a non-selection (not pressed) state, so that only one of buttons is selected (pressed) at all times. The checkbox is used to select a plurality of items from several options. The tap is used to switchably display documents so that the managed documents are displayed switchably by selecting the tap.

(4) In the aforementioned embodiment, the control element enables selection of a material is the dropdown list 10g as illustrated in FIG. 2. Alternatively, the combobox, the radio button, the checkbox, or the tap described above may also be employed as described above.

(5) In the aforementioned embodiment, the index includes the spatial resolution (CT image size) 10b and the density resolution (contrast) 10c as illustrated in FIG. 2. Alternatively, any two-dimensional index other than the spatial resolution or the density resolution may also be employed as long as it relates to image quality. For example, two parameters such as a dynamic range for expressing a brightness or color pattern range or a signal-to-noise (S/N) ratio regarding noise may be selected, and the selected parameters may be used as the two-dimensional index relating to image quality. Alternatively, any one of the spatial resolution or the density resolution may be selected, and another one of the dynamic range or the S/N ratio may be selected, so that the selected parameters may be used as the two-dimensional index relating to image quality.

(6) In the aforementioned embodiment, when the CT imaging condition is selected, the preview image 10d is displayed as an image view serving as a reference of the output image corresponding to the selected condition as illustrated in FIG. 2. However, it is not absolutely necessary to display the preview image. Anyway, it is preferable to display the preview image as in the aforementioned embodiment in order to check what type of output image is obtained without performing the CT imaging or the reconstruction process.

Figure 5:
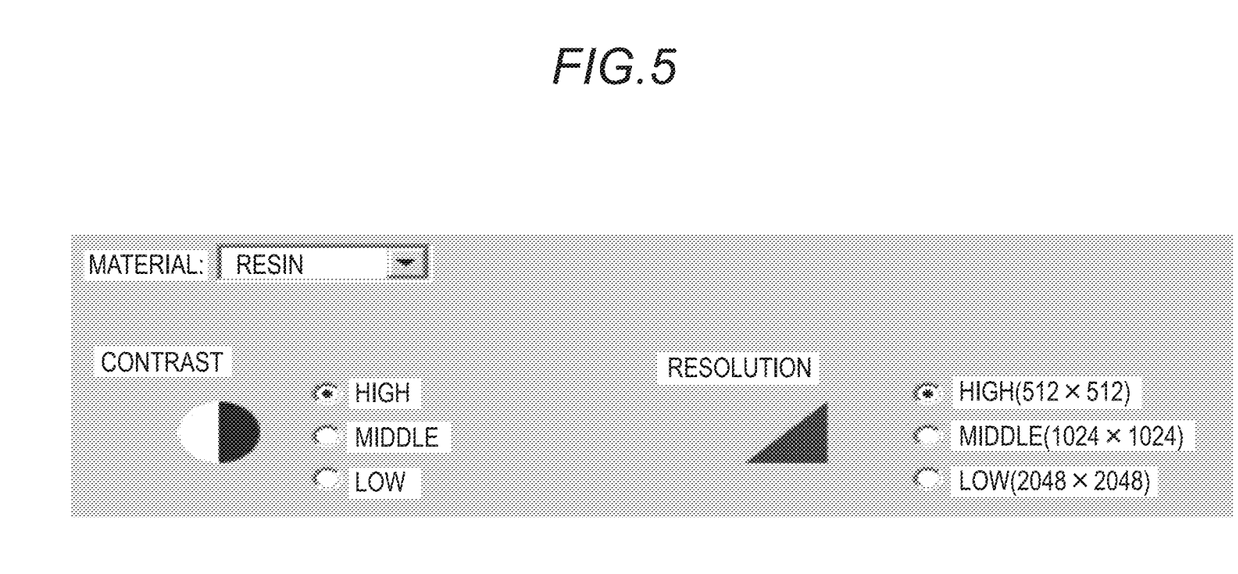
FIG. 5 illustrates a CT imaging condition setting screen of the display device according to a modification of the invention.

(7) In the aforementioned embodiment, the control elements as the icons 10a are arranged side by side in horizontal and vertical directions for each index (the spatial resolution 10b and the density resolution 10c) on the display screen (CT imaging condition setting screen 10A) as illustrated in FIG. 2. Alternatively, the control elements may be displayed independently for each index. For example, in a case where the index includes the spatial resolution (simply, resolution) and the density resolution (contrast) as in the aforementioned embodiment, a setting combination of the resolution and the contrast may be set for each imaging condition as illustrated in FIG. 5.

(8) In the aforementioned embodiment, the display device includes the imaging condition display means (imaging condition display unit 10e of FIG. 2) for displaying the set CT imaging condition. However, it is not absolutely necessary to provide the imaging condition display means (imaging condition display unit 10e). Alternatively, it is preferable to provide the imaging condition display means (imaging condition display unit 10e) as in the aforementioned embodiment in order to check the set CT imaging condition.

(9) In the aforementioned embodiment, the imaging condition input confirmation means used to perform an input operation for confirming the set CT imaging condition (the imaging condition input confirmation button 10f of FIG. 2) also serves as the imaging start button. Alternatively, separate buttons may be employed for each purpose. In order to prevent the CT imaging from being automatically performed even when the set CT imaging condition is not suitable, another imaging condition input confirmation means (imaging condition input confirmation button 10f) may be provided separately from the imaging start button. That is, it is checked whether or not the CT imaging condition is suitable. When a user determines that the imaging condition is optimum, an input operation to the imaging condition input confirmation means (imaging condition input confirmation button 10f) may be performed to confirm the CT imaging condition. Then, the CT imaging may be performed on the basis of the confirmed CT imaging condition when the imaging start button is pressed again.

(10) In the aforementioned embodiment, the control element (the dropdown list 10g of FIG. 2 in the aforementioned embodiment) enables selection of a material is further provided on the display screen. The CT imaging condition for each material corresponding to the selected control element (dropdown list 10g) is set when this control element (dropdown list 10g) is selected. However, it is not absolutely necessary to set the CT imaging condition for each material as long as the target object (work) is a single type.

(11) The display device may be configured such that a user can arbitrarily change or add the preset. In addition, the display device may be configured such that the content of the material can be arbitrarily changed, or the type of the material can be arbitrarily added. In this manner, the display device may be configured such that the registered CT imaging condition preset is editable.

As described above, the invention is suitable for an industrial X-ray CT device.

The invention claimed is:

1. A display device having a computer tomographic (CT) software function used in an X-ray CT device, comprising:
   control elements configured to register presets for a plurality of CT imaging conditions and arranged on a display screen using a two-dimensional index relating to image quality,
   wherein, as one of the control elements is selected, a CT imaging condition corresponding to the selected control element is set,
   wherein the control elements are sequentially arranged along a first axis according to a first index relating to image quality, and are sequentially arranged along a second axis according to a second index relating to image quality.

2. The display device according to claim 1, wherein the index includes a spatial resolution and a density resolution.

3. The display device according to claim 1, wherein, when the CT imaging condition is selected, a preview image is displayed as an image view serving as a reference of an output image corresponding to the selected condition.

4. The display device according to claim 1, wherein the control elements are icons arranged side by side across horizontal and vertical directions for each index on the display screen.

5. The display device according to claim 1, wherein the control elements are displayed independently for each index.

6. The display device according to claim 1, further comprising imaging condition display means configured to display the set CT imaging condition.

7. The display device according to claim 1, further comprising imaging condition input confirmation means configured to perform an input operation for confirming the set CT imaging condition,
   wherein CT imaging is performed on the basis of the confirmed CT imaging condition in response to the input operation to the imaging condition input confirmation means.

8. The display device according to claim 1, further comprising a control element that enables selection of a material on the display screen,
   wherein, when the control element is selected, a CT imaging condition is set for each material corresponding to the selected control element.

9. The display device according to claim 8, wherein the control element that enables selection of the material includes a dropdown list, a combobox, a radio button, a checkbox, or a tap.

10. The display device according to claim 1, wherein a preset of the registered CT imaging condition is configured editably.

11. An X-ray CT device comprising:
    an X-ray source that generates an X-ray for irradiating X-rays onto a target object;
    a stage for placing the target object;
    an X-ray detector that detects the X-ray irradiated from the X-ray source to the target object and transmitted through the target object;
    a display device having a CT software function including a function of setting a CT imaging condition; and
    a reconstruction processing unit that reconstructs a CT image of the target object from the data detected by the X-ray detector,
    wherein the display device comprises control elements configured to register presets for a plurality of CT imaging conditions and arranged on a display screen using a two-dimensional index relating to image quality, wherein, as one of the control elements is selected, a CT imaging condition corresponding to the selected control element is set, wherein the control elements are sequentially arranged along a first axis according to a first index relating to image quality, and are sequentially arranged along a second axis according to a second index relating to image quality.

* * * * *